United States Patent
Aoyagi et al.

(10) Patent No.: US 8,609,424 B2
(45) Date of Patent: Dec. 17, 2013

(54) ANTIBODY DIRECTED AGAINST PRO-GASTRIN RELEASING PEPTIDE, AND USE THEREOF

(75) Inventors: Katsumi Aoyagi, Saitama (JP); Yukiji Izawa, Saitama (JP)

(73) Assignee: Advanced Life Science Institute, Inc., Saitama (JP)

(*) Notice: Subject to any disclaimer, the term of this patent is extended or adjusted under 35 U.S.C. 154(b) by 441 days.

(21) Appl. No.: 12/739,952

(22) PCT Filed: Sep. 29, 2008

(86) PCT No.: PCT/JP2008/002716
§ 371 (c)(1),
(2), (4) Date: Apr. 26, 2010

(87) PCT Pub. No.: WO2009/054091
PCT Pub. Date: Apr. 30, 2009

(65) Prior Publication Data
US 2010/0248274 A1    Sep. 30, 2010

(30) Foreign Application Priority Data
Oct. 26, 2007 (JP) ................................ 2007-278843

(51) Int. Cl.
*G01N 33/68* (2006.01)
*G01N 33/53* (2006.01)

(52) U.S. Cl.
USPC ............................. 436/86; 435/7.94; 435/7.1

(58) Field of Classification Search
None
See application file for complete search history.

(56) References Cited

U.S. PATENT DOCUMENTS

| 4,208,479 | A | * | 6/1980 | Zuk et al. | 435/7.9 |
| 6,682,917 | B1 | * | 1/2004 | Nakamura et al. | 435/189 |

FOREIGN PATENT DOCUMENTS

| EP | 0 811 683 | A1 | * | 12/2007 | C12N 15/12 |
| EP | 1 876 445 | A1 | * | 1/2008 | G01N 33/53 |
| WO | WO 2006/117994 | | | 11/2006 | |

OTHER PUBLICATIONS

Fujirebio Diagnostics, Inc., Product Information Sheet for "CanAg ProGRP EIA", Jun. 2007, two pages, retrieved from http://www.fdi.com/documents/products/inserts/eia/ProGRP%20EIA,%20June%202007,%20r1.pdf on Aug. 13, 2012.*
Nordlund et al. "Automated time-resolved immunofluorometric assay for progastrin-releasing peptide" Clin Chem. May 2008;54(5):919-22.*
Nordlund et al. "Characteristics and clinical validity of two immunoassays for ProGRP" Tumor Biol. (2012) 33:1105-1113.*
The Academic Press Dictionary of Science and Technology (definition for the term "polyclonal"; Oxford: Elsevier Science & Technology (1996); retrieved Oct. 22, 2008, from http://www.credoreference.com/entry/3144515/.*
Janeway et al. Immunobiology: the Immune System in Health and Disease (1999), Elsevier Science Ltd/Garland Publishing, New York, NY, Fourth Edition, pp. 34-35.*
Harlow & Lane, "Antibodies: A Laboratory Manual", Cold Spring Harbor Laboratory, Cold Spring Harbor, NY, 1988, pp. 23-24 and 76.*
Wolfe, S.L., "Molecular and Cellular Biology", 1993, Wadsworth Publishing Company, Belmont, CA, pp. 790-793.*
Patel et al. "C-Terminal Fragments of the Gastrin-Releasing Peptide Precursor Stimulate Cell Proliferation via a Novel Receptor" Endocrinology 148(3):1330-1339, published online Nov. 22, 2006.*
Nordlund et al. "Production of New Monoclonal Antibodies to the Entire proGRP(1-125) Peptide", Tumor Markers, Clinical Oncology, Abstracts of the 35th Meeting of the International Society for Oncodevelopmental Biology and Medicine, Sep. 15-19, 2007, Poster Abstract No. P4_29, pp. 75 and 103.*
Nordlund et al. "Production of new monoclonal antibodies to the entire proGRP(1-125) peptide", poster No. P4_29 presented at The 35th Meeting of the International Society for Oncodevelopmental Biology and Medicine, ISOBM 2007, Sep. 15-19, 2007, Prague, Czech Republic.*
Patel et al. "C-Terminal Fragments of the Gastrin-Releasing Peptide Precursor Stimulate Cell Proliferation via a Novel Receptor" Endocrinology 148(3):1330-1339.*
Aoyagi et al., Clin. Chem. vol. 41, No. 4, pp. 537-543 (Apr. 1, 1995).
CanAg ProGRP ETA, Prod. No. 220-85, Fujirebio Diagnostics AB, Sep. 2007.
European Search Report for Application No. EP08841363, dated Sep. 8, 2011 (one page).

* cited by examiner

*Primary Examiner* — Christine Foster
(74) *Attorney, Agent, or Firm* — Edwards Wildman Palmer LLP; Peter F. Corless (57) ABSTRACT

Disclosed is a novel high-sensitive ProGRP measurement method, which is free from problems such as the fluctuations in measurement values and the operational constraints (e.g., the constraints on the handling of a sample). Specifically disclosed is a method for the measurement of a gastrin-releasing peptide precursor and/or a digested product thereof using at least two different antibodies each of which can recognize an epitope represented by the amino acid sequence consisting of amino acid 47 to amino acid 68 of the amino acid sequence set forth in SEQ ID NO:1. The method can detect a ProGRP or a digested product thereof in a refrigerated sample within a shorter period, by using the sample in a smaller amount, and with a higher degree of detective sensitivity, compared with the conventional methods.

5 Claims, 4 Drawing Sheets

[Bar chart titled "PGCY5" with y-axis "OD492/630" from 0.0 to 2.5 and x-axis "Amino Acid No." showing ranges from 31-38 to 91-98 in increments of 3. Peaks appear at 70-77 (~2.1) and 73-80 (~1.8), with smaller values at 67-74 and 76-83.]

Fig. 6

SEQ ID NO: 3
```
31                    50                    70                    90
STGESSSVSERGSLKQQLREYIRWEEAARNLLGLIEAKENRNHQPPQPKALGNQQPSWDSE
```

| ESSSVSER | QLREYIRWEEA | NRNHQPP | QQPSW |
| PGCY12 | PGCY17 | PGCY5 | GRP-3G2 |
| SEQ ID NO: 4 | SEQ ID NO: 5 | SEQ ID NO: 7 | SEQ ID NO: 8 |

EEAARNLLGLIEAK
PGCY9
SEQ ID NO: 6

ProGRP (34-57)

ProGRP (47-68)

ProGRP (55-76)

ProGRP (55-88)

ProGRP (70-88)

SEQUENCE LISTING

<160> NUMBER OF SEQ ID NOS: 8

<210> SEQ ID NO 1
<211> LENGTH: 98
<212> TYPE: PRT
<213> ORGANISM: Human

<400> SEQUENCE: 1

Val Pro Leu Pro Ala Gly Gly Gly Thr Val Leu Thr Lys Met Tyr Pro
1               5                   10                  15

Arg Gly Asn His Trp Ala Val Gly His Leu Met Gly Lys Lys Ser Thr
            20                  25                  30

Gly Glu Ser Ser Ser Val Ser Glu Arg Gly Ser Leu Lys Gln Gln Leu
        35                  40                  45

Arg Glu Tyr Ile Arg Trp Glu Glu Ala Ala Arg Asn Leu Leu Gly Leu
    50                  55                  60

Ile Glu Ala Lys Glu Asn Arg Asn His Gln Pro Pro Gln Pro Lys Ala
65                  70                  75                  80

Leu Gly Asn Gln Gln Pro Ser Trp Asp Ser Glu Asp Ser Ser Asn Phe
                85                  90                  95

Lys Asp

<210> SEQ ID NO 2
<211> LENGTH: 294
<212> TYPE: DNA
<213> ORGANISM: Human
<220> FEATURE:
<221> NAME/KEY: CDS
<222> LOCATION: (1)..(294)
<223> OTHER INFORMATION:

<400> SEQUENCE: 2 gtc ccg ctg cct gcg ggc gga ggg acc gtg ctg acc aag atg tac ccg      48
Val Pro Leu Pro Ala Gly Gly Gly Thr Val Leu Thr Lys Met Tyr Pro
1               5                   10                  15 cgc ggc aac cac tgg gcg gtg ggg cac tta atg ggg aaa aag agc aca      96
Arg Gly Asn His Trp Ala Val Gly His Leu Met Gly Lys Lys Ser Thr
            20                  25                  30

-continued

```
ggg gag tct tct tct gtt tct gag aga ggg agc ctg aag cag cag ctg    144
Gly Glu Ser Ser Ser Val Ser Glu Arg Gly Ser Leu Lys Gln Gln Leu
         35                  40                  45 aga gag tac atc agg tgg gaa gaa gct gca agg aat ttg ctg ggt ctc    192
Arg Glu Tyr Ile Arg Trp Glu Glu Ala Ala Arg Asn Leu Leu Gly Leu
 50                  55                  60 ata gaa gca aag gag aac aga aac cac cag cca cct caa ccc aag gcc    240
Ile Glu Ala Lys Glu Asn Arg Asn His Gln Pro Pro Gln Pro Lys Ala
 65                  70                  75                  80 ctg ggc aat cag cag cct tcg tgg gat tca gag gat agc agc aac ttc    288
Leu Gly Asn Gln Gln Pro Ser Trp Asp Ser Glu Asp Ser Ser Asn Phe
             85                  90                  95 aaa gat                                                            294
Lys Asp

<210> SEQ ID NO 3
<211> LENGTH: 61
<212> TYPE: PRT
<213> ORGANISM: Artificial Sequence
<220> FEATURE:
<223> OTHER INFORMATION: ProGRP(31-91)

<400> SEQUENCE: 3

Ser Thr Gly Glu Ser Ser Ser Val Ser Glu Arg Gly Ser Leu Lys Gln
1               5                   10                  15

Gln Leu Arg Glu Tyr Ile Arg Trp Glu Glu Ala Ala Arg Asn Leu Leu
            20                  25                  30

Gly Leu Ile Glu Ala Lys Glu Asn Arg Asn His Gln Pro Pro Gln Pro
        35                  40                  45

Lys Ala Leu Gly Asn Gln Gln Pro Ser Trp Asp Ser Glu
    50                  55                  60

<210> SEQ ID NO 4
<211> LENGTH: 8
<212> TYPE: PRT
<213> ORGANISM: Artificial Sequence
<220> FEATURE:
<223> OTHER INFORMATION: PGCY12 epitope sequence

<400> SEQUENCE: 4

Glu Ser Ser Ser Val Ser Glu Arg
1               5

<210> SEQ ID NO 5
<211> LENGTH: 11
<212> TYPE: PRT
<213> ORGANISM: Artificial Sequence
<220> FEATURE:
<223> OTHER INFORMATION: PGCY17 epitope sequence

<400> SEQUENCE: 5

Gln Leu Arg Glu Tyr Ile Arg Trp Glu Glu Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: PGCY9 epitope sequence

<400> SEQUENCE: 6

Glu Glu Ala Ala Arg Asn Leu Leu Gly Leu Ile Glu Ala Lys
1               5                   10
```

```
<210> SEQ ID NO 7
<211> LENGTH: 7
<212> TYPE: PRT
<213> ORGANISM: Artificial Sequence
<220> FEATURE:
<223> OTHER INFORMATION: PGCY5 epitope sequence

<400> SEQUENCE: 7

Asn Arg Asn His Gln Pro Pro
1               5

<210> SEQ ID NO 8
<211> LENGTH: 5
<212> TYPE: PRT
<213> ORGANISM: Artificial Sequence
<220> FEATURE:
<223> OTHER INFORMATION: GRP-3G2 epitope sequence

<400> SEQUENCE: 8

Gln Gln Pro Ser Trp
1               5
```

ANTIBODY DIRECTED AGAINST PRO-GASTRIN RELEASING PEPTIDE, AND USE THEREOF

RELATED APPLICATION

This application is the U.S. national phase, pursuant to 35 U.S.C. §371, of PCT international application Ser. No. PCT/JP2008/002716, filed Sep. 29, 2008, designating the United States, which claims priority to Japanese Patent Application No. 2007-278843, filed Oct. 26, 2007. The entire contents of the aforementioned patent applications are incorporated herein by this reference.

TECHNICAL FIELD

The present invention relates to antibodies directed against gastrin releasing peptide precursor (ProGRP) and use thereof, and is widely used in the early discovery, monitoring of treatment, monitoring of reoccurrence, or the like of various diseases including small-cell lung carcinoma.

BACKGROUND ART

The leading cause of death in Japan is malignant neoplasm, and among others, the mortality of lung cancer overtakes that of stomach cancer to rank the first in men, while ranking the third in women. The mortality of lung cancer tends to increase every year. Lung cancer is histopathologically classified into the following four main tissue types: lung squamous-cell carcinoma and small-cell lung carcinoma (SCLC) developing in the hilar area of the lung, and lung adenocarcinoma and large-cell lung carcinoma developing in the lung field.

In particular, small-cell lung carcinoma rapidly proliferates and causes remote metastasis in the early stage, and therefore, in many cases, this carcinoma is discovered to be advanced cancer, which has already metastasized systemically, even at the time of initial diagnosis. In regard to the cure rate of this type of cancer, the cure rate in patients with limited disease (LD) small-cell lung carcinoma in which the lesion is limited only to one side of the lung field is approximately 20%; however, inpatients with extensive disease (ED) small-cell lung carcinoma in which the lesion has metastasized to both lungs or to other organs, cure is said to be practically difficult.

Furthermore, since small-cell lung carcinoma is highly sensitive to anticancer drugs, chemotherapy is considered as the first choice of therapy. On the contrary, non-small-cell lung carcinoma (non-SCLC) shows a low response rate for chemotherapy, and thus surgical therapy is considered as the first choice of therapy.

Therefore, small-cell lung carcinoma is a cancer which particularly necessitates early discovery and treatment even among various types of lung cancers, and for that reason, differential diagnosis of small-cell lung carcinoma and non-small-cell lung carcinoma is extremely important for making decision on the therapeutic strategy.

One of the methods for detecting lung cancer is the sputum examination. However, although the sputum examination is suitable mainly for the examination of lung squamous-cell carcinoma, there is a problem that the positive rate against small-cell lung carcinoma is low. Roentgenography is also a method widely used in the discovery of lung cancer, but concerning the lung squamous-cell carcinoma or small-cell lung carcinoma developing in the hilar area of the lung, there is a problem that the shadow of the heart falls on the hilar area, so that it is very difficult to take images of the shadow of cancerous tissues. Further, with regard to small-cell lung carcinoma, it is considered that even if those patients showing abnormal shadow of the lung field are diagnosed using sputum cytodiagnosis, simple chest roentgenography, CT scan, bronchoscopy and the like, early discovery of this type of lung cancer is not easy.

In addition, some of the testing methods for diagnosing cancer such as, for example, exposure to radiation, biopsy and bronchoscopy, cause pain in the patients, and also require highly expensive equipments, expert technology, and the like.

Therefore, research is being conducted to find a tumor marker which makes it possible, through a more convenient blood test, to diagnose cancer with high efficiency while the cancer is curable. Today, 30 or more tumor markers are being utilized in the discovery and diagnosis of cancer diseases, indication for monitoring the course of disease, diagnosis of recurrence, and the like.

Since lung cancer is classified into a variety of tissue types, a tumor marker which is effective for the discovery or diagnosis of all types of lung cancer, is not reported yet. Therefore, at present, effective markers are selected and used in accordance with each tissue type of lung cancer.

For instance, carcinoembryonic antigen (CEA) or sialyl Lex-i antigen is mainly selected and used for lung adenocarcinoma, while squamous-cell carcinoma related antigen (SCC) is mainly selected and used for lung squamous-cell carcinoma, and so is neuron-specific enolase (NSE) or the like for small-cell lung carcinoma.

However, NSE is disadvantageous in that: (1) the positive rate against curable early cancer is low; (2) a transient increase in the measured values due to treatment is recognized; (3) the measured values are increased due to hemolysis upon blood collection; and (4) the difference between the measured values obtained from small-cell lung carcinoma patients and the measured values obtained from normal persons is small. Therefore, NSE could not be necessarily said to be an effective tumor marker for small-cell lung carcinoma.

Gastrin-releasing peptide (GRP) is a brain-gut peptide composed of 27 amino acids, which was isolated from porcine stomach tissues by McDonald et al. in 1978, and has a gastrin secretion promoting action. The existence of GRP in human has also been confirmed, and a gene encoding human GRP was also cloned in 1984.

Yamaguchi et al. at the National Cancer Center in Japan conducted an investigation on the biological characteristics of small-cell lung carcinoma, which is thought to be derived from neuroendocrine cells, and in the course of the investigation, they examined 15 or more kinds of brain-gut hormones, including adrenocorticotropic hormone (ACTH), calcitonin and the like, and found that GRP is actively secreted from cultured small-cell lung carcinoma cell lines at the highest frequency and highest concentration (Non-Patent Document 1). They also established a radioimmunoassay (RIA) combined with a method for concentrating GRP in blood, and revealed that patients with small-cell lung carcinoma would exhibit higher blood GRP concentration as compared with healthy persons. However, since GRP is rapidly digested in the blood, concentration thereof in blood is low, and since the assay mentioned above requires a complicated concentration process, clinical application of the assay is difficult.

It was revealed by researches conducted thereafter that three species of GRP precursors (ProGRP) are produced in various cells by alternative RNA splicing (Non-Patent Document 2). These three species of ProGRP have in common from amino acid 1 to amino acid 98 of the amino acid sequence, while the amino acid sequence varies among one another, from amino acid 99 and the rest, because of alternative RNA splicing. This common portion of the amino acid sequence consisting of amino acid 1 to amino acid 98 is shown in SEQ ID NO: 1. Hereinafter, in the invention, unless stated otherwise in particular, the number indication of amino acid residues in ProGRP, partial sequences thereof, digests and the like, is based on the number indication of the amino acid sequence of SEQ ID NO: 1.

The amino acid sequence consisting of amino acid 1 to amino acid 27 of the three species of ProGRP is identical with the amino acid sequence of mature GRP having gastrin secretion promoting activity. These three species precursors are all digested by hormone precursor cleavage enzymes, into mature type GRP having an amino acid sequence consisting of amino acid 1 to amino acid 27, and a C-terminal fragment (ProGRP-Cfrag) which is a digested product of ProGRP having an amino acid sequence consisting of amino acid 31 and the rest, and having no gastrin secretion promoting activity.

Holst et al. (Non-Patent Document 3) reported that according to a radioimmunoassay (RIA) method making use of an antiserum directed against a peptide having an amino acid sequence consisting of amino acid 42 to amino acid 53 (hereinafter, referred to as ProGRP (42-53)), the level of ProGRP or ProGRP-Cfrag in the blood plasma of patients with small-cell lung carcinoma was high. However, in this method, precipitation and extraction processes were required, and the sensitivity was not sufficient.

Miyake et al. noted that ProGRP is more stable in the blood than GRP, and that an amino acid sequence consisting of amino acid 31 to amino acid 98, which is a common portion in the three species of ProGRP, does not show homology with the amino acid sequences of other proteins, and thus they established a highly sensitive RIA method which does not require precipitation and extraction processes, using an antiserum with a high titer obtained by using a recombinant peptide formed from the same amino acid sequence (hereinafter, referred to as ProGRP (31-98)) as an antigen (Non-Patent Document 1). It was shown by this method that Pro-GRP serves as an excellent tumor marker in the same manner GRP does.

However, although this method is advantageous in the aspect of not requiring an extraction process, the measurement requires a period of 4 days, and the sensitivity is insufficient, being only 10 pM (77.3 pg of antigen/mL). Accordingly, the ProGRP level in the blood serum of a normal person cannot be measured, and this method is not satisfactory yet for clinical application.

Furthermore, since the RIA methods of Holst et al. and of Miyake et al. as described above are inhibition methods, measurement can be made if even a portion of a fragment of ProGRP has antigenicity. However, the sensitivity is lower than that of sandwich methods, and it is difficult to achieve clinical application of the ProGRP measuring methods where sensitivity enhancement is required. That is, in order to lead the detection of ProGRP to clinical application, it is essential to increase the sensitivity of detection, and particularly, an antibody that can be used in sandwich methods is needed.

Yamaguchi, Aoyagi et al. developed, for the purpose of achieving clinical application of ProGRP as a tumor marker for small-cell lung carcinoma, a convenient and highly sensitive reagent for ProGRP measurement which is based on the principle of enzyme-linked immunosorbent assay (ELISA) and makes use of a sandwich method (Patent Document 1). This method gives results in about 2 hours and has high sensitivity (2 pg/mL). Therefore, the method is at present widely used in clinical applications, and it is clear that Pro-GRP has higher sensitivity and specificity to small-cell lung carcinoma as compared with NSE.

It was also found using this measurement method that the serum ProGRP levels also increased in neuroendocrine tumors (thyroid medullary cancer, and the like) and cancers exhibiting neuroendocrine tumor-like characteristics (esophageal small-cell carcinoma, pancreatic small-cell carcinoma, prostate small-cell carcinoma, and the like) as well as in small-cell lung carcinoma. Thus, it is conceived that this method will be applied to early discovery of these tumors or monitoring of the treatment in the future.

However, although the stability of ProGRP in the blood is higher than that of GRP, more fluctuation in the measured values is recognized as compared with other common tumor markers. Therefore, in those methods using ProGRP as the object of detection, there is a restriction that the test sample for measurement must be frozen from immediately after the collection of blood to the time of measurement and stored (Non-Patent Document 4).

Aoyagi developed a sandwich measurement method making use of two or more species of antibodies that recognize the amino acid residue 40 to amino acid residue 75 of ProGRP or the amino acid residue 40 to amino acid residue 79 of Pro-GRP, which are both internal regions of ProGRP (31-98) (Patent Document 3). This method gives relatively stable results by measuring a test sample which has been stored at 4° C., and exhibits a detection sensitivity that is almost equal to that of the method described in Patent Document 2. However, this method requires, as shown in Example 4 of Patent Document 3, an amount of test sample that is more than that of common immunoassay methods, which use an amount of 100 µL.

Patent Document 1: Japanese Patent No. 3210994
Patent Document 2: Japanese Patent Application Laid-Open (JP-A) No. 6-98794
Patent Document 3: WO 2006/117994
Non-Patent Document 1: Cancer Research, Vol. 54, pp. 2136-2140 (1994)
Non-Patent Document 2: Spindel, et al., Mol. Endocrinol., Vol. 1, pp. 224-232 (1987)
Non-Patent Document 3: Holst, et al., J. Clin. Oncol., Vol. 7, 1831-1838 (1989)
Non-Patent Document 4: RinshoKensa, Vol. 39, pp. 981-986 (1995)

DISCLOSURE OF THE INVENTION

Problem to be Solved by the Invention

In regard to the method described in Patent Document 3, if the required amount of test sample can be decreased to a smaller amount while the detection sensitivity is maintained, it is possible to achieve cutdown of the cost necessary for the measurement or reduction of patient burden in clinical practice. Furthermore, a measurement method in which the decrease in the measurement sensitivity due to storage of the test sample is smaller, can make the handling of the test sample more convenient. The present invention is intended to provide a new method for measuring ProGRP, which exhibits less reduction of the detection sensitivity despite storage of the test sample, and enables measurement with a smaller amount of test sample.

Means for Solving the Problem

The present invention is based on a discovery that an immunoassay method making use of an antibody to a specific region of ProGRP can solve the problems described above, and thus the following respective inventions were completed.

(1) A method for measuring a gastrin-releasing peptide precursor and/or a digested product thereof, using two or more different antibodies which recognize an epitope represented by an amino acid sequence consisting of amino acid 47 to amino acid 68 of the amino acid sequence set forth in SEQ ID NO: 1.

(2) The method according to (1), which is a sandwich immunoassay method.

(3) A monoclonal antibody capable of recognizing an epitope represented by an amino acid sequence consisting of amino acid 47 to amino acid 68 of the amino acid sequence set forth in SEQ ID NO: 1.

(4) The monoclonal antibody according to (3), which is produced by hybridoma GCY9 deposited under Accession No. FERM P-21308.

(5) The monoclonal antibody according to (3), which is produced by hybridoma GCY17 deposited under Accession No. FERM P-21309.

(6) Hybridoma GCY9 deposited under Accession No. FERM P-21308.

(7) Hybridoma GCY17 deposited under Accession No. FERM P-21309.

(8) The method according to (1), wherein at least one of the two or more different antibodies is the antibody according to (4) or (5).

(9) A kit for measuring a gastrin releasing peptide precursor or a digested product thereof, including the antibody according to any one of (3) to (5).

(10) The kit according to (9), which is a kit for diagnosing cancer or monitoring the effects of treatment of cancer.

Effect of the Invention

The method of the present invention offers effects such as that a detection sensitivity equivalent to that of conventional measurement methods can be obtained, as well as that the method is hardly affected in terms of handling of the test sample after collection, and that highly reproducible measured values may be obtained, by taking a digested product of ProGRP which has been stably stored even in a test sample, as an object of measurement. Thereby, at a clinical site of collecting a test sample of blood for the diagnosis of diseases such as small-cell lung carcinoma, handling of the test sample after the collection of blood becomes easier, and the measured values for ProGRP are no longer subject to fluctuation, so that more stable results are obtained, and the reliability of the measured values is increased. Furthermore, in the case where there occurs a request for additional tests or a need for reexamination based on clinical manifestations, or the like, measurement making use not of a test sample that has been stored frozen, but of a test sample that has been stored in refrigeration, is made possible, so that the cost necessary for the measurement can be cut down. The method of the present invention also makes it possible to reduce the amount of test sample to be measured and to shorten the measurement time, while maintaining high detection sensitivity, and can cut down the costs recurring in clinical situations and reduce patient burden.

BEST MODES FOR CARRYING OUT THE INVENTION

The present invention is a method of detecting ProGRP or a digested product of ProGRP having from amino acid residue 47 to amino acid residue 68 of ProGRP, according to a sandwich immunoassay method, using two or more different antibodies capable of recognizing an epitope represented by an amino acid sequence consisting of amino acid 47 to amino acid 68 of ProGRP. This immunoassay method is characterized in that even when a collected test sample is stored in refrigeration, the detection sensitivity is not decreased. This is speculated to mean that the digested product of ProGRP having the amino acid residue 47 to amino acid residue 68 of ProGRP is relatively stable to new digestive reactions occurring during the storage of test sample due to the proteases contained in the test sample or other causes.

The antibody that can be used in the method of the present invention is an antibody that can recognize an epitope represented by an amino acid sequence consisting of amino acid 47 to amino acid 68 of ProGRP, and can thereby bind to a digested product of ProGRP having from amino acid residue 47 to amino acid residue 68 of ProGRP. Such an antibody is preferably a monoclonal antibody.

The antibody that can be used in the method of the present invention is preferably two or more different monoclonal antibodies that are capable of recognizing an epitope present at the N-terminal region and an epitope present at the C-terminal region in the amino acid sequence consisting of amino acid 47 to amino acid 68 of ProGRP. In particular, it is particularly preferable to use PGCY9 and PGCY17, which are monoclonal antibodies produced by hybridoma GCY9 deposited under Accession No. FERM P-21308 and hybridoma GCY17 deposited under Accession No. FERM P-21309, both deposited with the International Patent Organism Depositary at the National Institute of Advanced Industrial Science and Technology. These two types of hybridoma cells are hybridoma cells prepared by a conventional method from the antibody-producing cells of mice which have been immunized with a polypeptide having an amino acid sequence consisting of amino acid 31 to amino acid 98 of a recombinant ProGRP produced using *Escherichia coli* (hereinafter, indicated as ProGRP (31-98)) as an antigen, and are cells producing an antibody that recognizes an epitope represented by amino acid 47 to amino acid 68 of ProGRP, which has been selected by screening using peptides within ProGRP (31-98).

As such, the antibody used in the present invention can be obtained by preparing hybridoma cells which produce a monoclonal antibody by a conventional method, from antibody-producing cells that are recovered after immunizing an experimental animal such as mouse, rat, guinea pig, rabbit, chicken, goat, sheep or cattle using ProGRP (31-98) as an antigen, and screening hybridoma cells that produce a desired antibody, using a polypeptide consisting of amino acid residue 47 to amino acid residue 68 of ProGRP (hereinafter, indicated as ProGRP (47-68)). ProGRP (47-68) may also be used as an antigen. The aforementioned polypeptide may also be used while being bound to a support such as cycloglobulin or keyhole limpet hemocyanine.

The method for immunizing an animal will be described by taking an example of mouse. A polypeptide such as ProGRP (31-98) is mixed with an adjuvant such as Freund's complete adjuvant or TITER MAX™ Gold (CytRx Corp.) at a ratio of 1:1, and the mixture is repeatedly passed through the joint of two syringes joined by a cross-flow joint, or is subjected to ultrasonication to thereby prepare an emulsion. The prepared antigen-containing emulsion is injected at any of subcutaneous, intradermal, intramuscular and interperitoneal sites, or at multiple sites. After completion of the initial immunization, booster immunization is similarly carried out at an interval of 1 to 4 weeks. Thereafter, immunization is continued in the same manner, until the antibody titer of the antibody directed against ProGRP (31-98) in the blood increases.

Measurement of the antibody titer can be carried out as follows. ProGRP (31-98) is dissolved in PBS to a concentration of 1 μg/mL, and the solution is added to each well of a 96-well microtiter plate at a volume of about 50 μL per well, so that the peptide is adsorbed overnight at 4° C. Each well is washed with PBS supplemented with 0.05% TWEEN 20™ (polyoxyethylene (20) sorbitan monolaurate) (PBS-T), and then is used for assay. Prior to the assay, blocking may be carried out with PBS containing 1% BSA, or the like. Blood is collected from the orbital venous plexus, caudal vein, caudal artery or the like, and the blood is diluted 30-fold with PBS-T and then centrifuged. The resulting supernatant is used to prepare a series of dilutions with PBS-T, and 50 μL each thereof is added to each well of the microtiter plate coated with ProGRP (31-98). The peptide is allowed to react for 30 minutes at room temperature, and then the plate is washed with PBS-T. 50 μL each of a horseradish peroxidase (HRP)-labeled anti-mouse IgG solution which has been appropriately diluted with PBS-T is added to each well. The plate is further incubated for 30 minutes at room temperature, and then hydrogen peroxide and an ortho-phenylenediamine substrate solution is added to react for 30 minutes. 50 μL of 2N $H_2SO_4$ is added to terminate the reaction, and the absorbance of each well is measured.

After it is confirmed that the antibody titer against the administered antigen has sufficiently increased in the immunized mouse, the spleen is extracted, and the spleen cells are isolated. These cells are fused with mouse myeloma cells (for example, SP2/0-Ag14, or the like) that have been separately cultured, using polyethylene glycol or the like. Those successfully fused cells are selectively cultured in HAT (hypoxanthine-aminopterin-thymidine) medium. Culture is continued for about 7 to 14 days, while half the volume of the medium is exchanged every several days, and then the antibody titer of the cultured supernatant is measured. The cells of positive wells are cloned by a limiting dilution method, and thus a hybridoma producing the target antibody is obtained.

When the epitope of the antibody obtained by the method described above is determined, an antibody which recognizes the epitope represented by the amino acid sequence consisting of amino acid 47 to amino acid 68 of ProGRP, can be obtained. Epitope analysis can be carried out by examining the reaction of the antibody directed against a polypeptide having a contiguous sequence of 8 to 12 amino acids of ProGRP (31-98) which has been prepared by the multipin peptide synthesis method, or ProGRP (47-68). The epitope can be determined by, for example, coating a microtiter plate with ProGRP (47-68) which has been recombinantly expressed, or with ProGRP (47-68) which has been chemically synthesized by the Fmoc method or Boc method, and examining the reactivity of the antibody to the respective peptides by the immunoassay method previously described.

As a result of the epitope analysis using the polypeptide having a contiguous sequence of 8 to 12 amino acids of ProGRP (31-98) prepared by the multipin peptide synthesis method, it was confirmed that PGCY9, which is one of the antibodies particularly preferred in the present invention, is a monoclonal antibody capable of recognizing an epitope represented by an amino acid sequence consisting of amino acid 55 to amino acid 66, among the epitopes represented by the amino acid sequence consisting of amino acid 47 to amino acid 68 of ProGRP. It was also confirmed that PGCY17, which is another antibody particularly preferred in the present invention, is a monoclonal antibody capable of recognizing at least an epitope represented by an amino acid sequence consisting of amino acid 45 to amino acid 57.

It is also possible to immobilize the antibody used in the present invention on a support or a microplate, or to label the antibody with an appropriate labeling reagent such as biotin. The respective processes of immobilization and labeling may be carried out according to the methods described in various manuals for experimental techniques, and an operation characteristic to the antibody used in the present invention is not considered particularly necessary.

The method of the present invention is a sandwich immunoassay method making use of the antibody mentioned above, and more specifically, a sandwich ELISA method. The fundamental operation of the sandwich ELISA method can be carried out according to the methods described in "Ultrasensitive Immunoassay" (Ishikawa Eiji, Japan Scientific Societies Press, 1993) or other various manuals for experimental techniques, and no special operation is considered particularly necessary in implementing the present invention. However, the method can be carried out by a process such as shown below.

That is, ProGRP and/or a digested product thereof can be detected according to a measurement method including (1) a process for reacting a first antibody that is capable of recognizing the epitope represented by the amino acid sequence consisting of amino acid 47 to amino acid 68 of ProGRP, with ProGRP and/or a digested product thereof in a test sample; (2) a process for reacting the ProGRP and/or a digested product thereof captured by the antibody, with a second antibody that is different from the antibody of (1) but is capable of recognizing the epitope represented by the amino acid sequence consisting of amino acid 47 to amino acid 68 of ProGRP; and (3) a process for detecting an immunocomplex developed by (2).

An example of the procedure of the method of the present invention can be described as follows. A solution prepared by dissolving a first antibody in a buffer solution, for example, a 0.1 M carbonate buffer solution (pH 9.6), to a concentration of about 1 to 10 μg/mL, is placed in each well of a microtiter plate in equal amounts, and the microtiter plate is incubated overnight at 4° C. Each well is washed with a buffer solution for washing such as PBS, and then the inner wall of each well which is not bound by the first antibody, is blocked by incubating for several hours using a buffer solution containing an appropriate protein such as casein sodium. After the blocking solution is removed, a reaction solution containing a surfactant such as TWEEN 20™ (polyoxyethylene (20) sorbitan monolaurate) and a test sample are added to each well. The amount of addition of the test sample is appropriately varied in accordance with the sensitivity of the measurement method. The reaction is performed for about one hour at a temperature of about 37° C., and then each well is washed with a buffer solution containing a surfactant (for example, PBS-T containing TWEEN 20™, polyoxyethylene (20) sorbitan monolaurate). A second antibody which has been labeled with an appropriate labeling reagent is added to each well and is allowed to react for several ten minutes. Subsequently, each well is washed, and the second antibody is detected by an appropriate method according to the labeling reagent. Here, this procedure described above is only an example after all, and the details of the operation of each stage, for example, the buffer solution, labeling reagent, amount of addition and the like, can be appropriately adjusted.

The detection sensitivity of the method of the present invention which uses two types of monoclonal antibodies, that is, monoclonal antibodies PGCY9 and PGCY17, is 2.5 pg/mL, and an amount of test sample of about 25 μL may be used. This detection sensitivity makes it possible to measure the level of ProGRP in blood in almost every normal person, and contributes to the cutdown of the cost for examination and reduction of patient burden in clinical practice.

The present invention also provides, in addition to the method described above, a kit for measuring ProGRP or a digested product thereof in a test sample, and particularly a diagnostic kit for conducting a diagnosis of small-cell lung carcinoma or monitoring of chemotherapy by measuring ProGRP and/or a digested product thereof. Such a kit includes at least two antibodies which recognize the epitope represented by amino acid 47 to amino acid 68 of ProGRP, and may also include in addition any of a reaction buffer solution or a dilution of a secondary antibody, a standard substance of ProGRP, instructions and other constituents. Preferred examples of the antibody included in the kit include two or more different antibodies which recognize the epitope represented by amino acid 47 to amino acid 68 of ProGRP, and representative examples include monoclonal antibody PGCY9 and monoclonal antibody PGCY17.

In regard to the antibody that binds to ProGRP and/or a digested product thereof, it is preferable to select and use only those antibodies that recognize the epitope represented by the amino acid sequence consisting of amino acid 47 to amino acid 68 of ProGRP, but an antibody other than such antibodies may also be included in the measurement system to the extent that measured values with high reproducibility can be obtained.

Hereinafter, the present invention will be further described by way of Examples.

EXAMPLES

Example 1

A recombinant was produced by the method described in Example 1 of Japanese Patent No. 3210994, and a polypeptide having the amino acid sequence set forth in SEQ ID NO: 1, which was expressed by *Escherichia coli*, was purified. In Example 1 of Japanese Patent No. 3210994, this recombinant protein is described as GRP (31-98); however, to be exact, since it is the (31-98) portion of GRP precursor (ProGRP), the recombinant protein will be described herein as ProGRP (31-98).

An antigenic protein prepared by coupling ProGRP (31-98):porcine thyroglobulin (TG) at a weight ratio of 1:3 (indicated as ProGRP-TG), was diluted with a 100 mM phosphate buffer solution (pH 6.0) containing 0.15 M NaCl, and was mixed with an equal amount of TITER MAX™ to obtain a ProGRP-TG suspension. The suspension prepared to achieve a concentration of ProGRP (31-98) of 0.05 mg/0.1 mL, was intraperitoneally administered 4 to 6 times at an interval of about 20 days, to a BALB/c mouse that was 4 to 6 weeks old. After about 4 more weeks, a physiological saline solution prepared to a ProGRP (31-98) concentration of 0.1 mg/0.1 mL was administered for two days as booster immunization. Three days after the final booster immunization, spleen was aseptically extracted from this immunized animal and was prepared into slices with scissors, and the spleen slices were further resolved into individual cells using a mesh, and the cells were washed three times with RPMI-1640 medium and then cultured for several days in the same medium containing 8-azaguanidine. Mouse myeloma cell line SP2/0-Ag14 in its logarithmic growth phase, from which revertant had been completely eliminated, was washed with RPMI-1640 medium, and then $2.4 \times 10^7$ cells of the cell line and $2.0 \times 10^8$ cells of the spleen cell sample mentioned above were placed in a centrifugal tube and mixed. The mixed two types of cells were subjected to centrifugation for 5 minutes at 200×g to remove the supernatant, and then were subjected to cell fusion using HVJ Envelop Cell Fusion Kit (GENOMEONE™-CF, Ishihara Sangyo Kaisha, Ltd.). The fused cells were diluted with RPMI-1640 medium containing hypoxanthine, aminopterin, thymidine (hereinafter, the 3 kinds of compounds are collectively indicated as HAT), 10% fetal calf serum (FCS) and mouse interleukin 6 (R&D Systems), and the dilution was added to a 96-well plate and cultured for 1 to 2 weeks. After about 1 to 2 weeks of culture, an ELISA method was carried out using ProGRP (31-98) as an antigen, and thereby a hybridoma which produces the monoclonal antibody of the present invention having specific reaction to ProGRP (31-98), was obtained.

The obtained hybridoma was subjected to screening for a cell line producing the desired antibody using ProGRP (31-98) and monoclonization according to a conventional limiting dilution method, and thus finally five hybridoma cell lines were obtained, which were designated as GCY9, GCY17, GCY12, GCY24 and GCY5, respectively. GCY9 and GCY17 are deposited with the International Patent Organism Depositary at the National Institute of Advanced industrial Science and Technology, Central 6, 1-1-1, Higashi, Tsukuba-city, Ibaraki, Japan, as of Jun. 22, 2007 (Accession No. of GCY9: FERM AP-21308, Accession No. of GCY17: FERM AP-21309). Furthermore, GCY9 and GCY17 are internationally deposited respectively as of Aug. 5, 2008 (International Accession No. of GCY9: FERM BP-10991, International Accession No. GCY17: FERM BP-10992).

Example 2

(1) The hybridomas obtained by the method described in Example 1 were cultured in a serum-free medium (Hybridoma-SFM, Invitrogen, Inc.) containing mouse interleukin 6, and the monoclonal antibodies thus produced were purified and recovered using a Protein A-bound Sepharose column (Amersham). The monoclonal antibodies produced from the respective hybridomas GCY9, GCY17, GCY12, GCY24 and GCY5 were designated as PGCY9, PGCY17, PGCY12, PGCY24 and PGCY5, respectively. In regard to the subtypes of PGCY9, PGCY17, PGCY12, PGCY24 and PGCY5, it was found by an experiment utilizing a rabbit anti-mouse Ig various-subtype kit (Zymed Laboratories, Inc.) that PGCY9, PGCY12, PGC24 and PGCY5 were of the IgG1 subtype, while PGCY17 was of the IgG2a subtype.

(2) Sixty-one species in total of polypeptides including 8 contiguous amino acids, which had been prepared with one amino acid being shifted in each polypeptide, were prepared by the multipin peptide synthesis method, based on the amino acid sequence of ProGRP (31-98). Each of the peptides was conjugated with biotin at the N-terminus. Each of the biotinylated polypeptides was dissolved in dimethylformamide, and the solution was diluted with PBS to a concentration of 1 µg/mL. The diluted solution of each biotinylated polypeptide was added to each avidin-immobilized well of a 96-well microtiter plate in an amount of 100 µL, and the plate was incubated overnight at 4° C. Each well was washed with PBS containing 0.05% TWEEN 20™ (polyoxyethylene (20) sorbitan monolaurate) (PBS-T), and then a solution prepared by diluting each monoclonal antibody to 1 µg/mL was added to each well in an amount of 100 µL. After the plate was allowed to react for 30 minutes at room temperature, each well was washed five times with PBS-T, and 100 µL of a horseradish peroxide (HRP)-labeled anti-mouse IgG antibody solution was added to each well. The plate was further allowed to react for 30 minutes at room temperature, and then each well was washed five times with PBS-T. A substrate solution (a 0.1 M citrate phosphate buffer solution containing 2 mg/mL of ortho-phenylenediamine and 0.9 µL/mL of a 30% aqueous solution of hydrogen peroxide, pH 5.0) was added to each well in an amount of 100 µL, and the plate was allowed to react for 30 minutes at room temperature. Subsequently, 100 µL of 2 N sulfuric acid was added to each well, and immediately, the absorbance at 492 nm was measured. The respective reactions of the monoclonal antibodies PGCY9, PGCY17, PGCY24, PGCY12 and PGCY5 against various peptides within ProGRP (31-98) are presented in FIG. 1 to FIG. 5.

Figure 1:
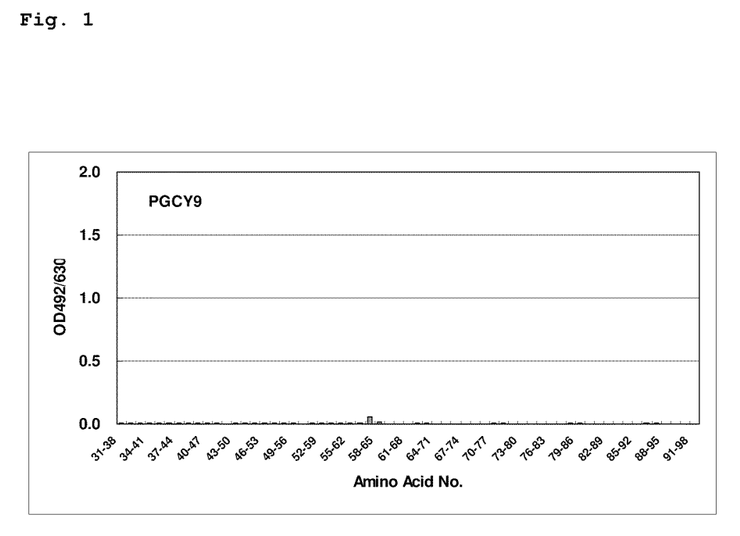
FIG. 1 is a graph showing the binding ability of monoclonal antibody PGCY9 to various polypeptides each having a contiguous sequence of 8 amino acids prepared by multipin peptide synthesis. The horizontal axis represents the various polypeptides and the numbers of amino acid residues in SEQ ID NO: 1, while the vertical axis represents absorbance.
Figure 2:
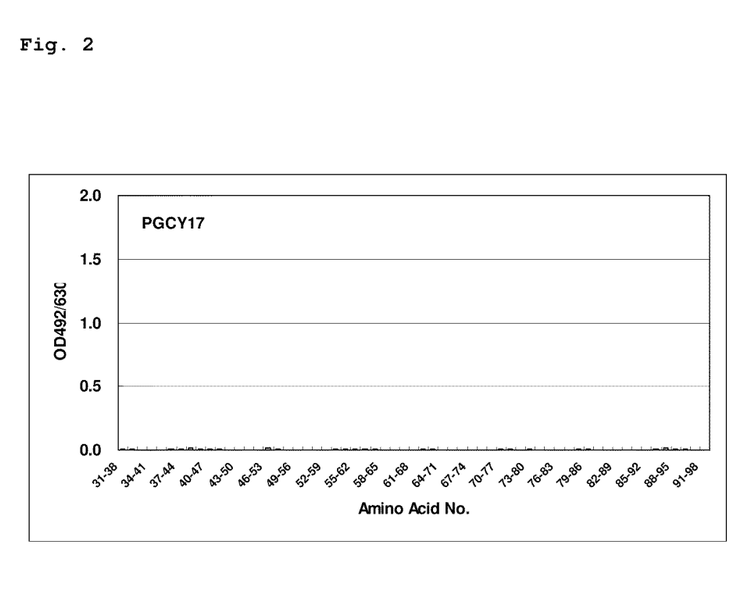
FIG. 2 is a graph showing the binding ability of monoclonal antibody PGCY17 to various polypeptides each having a contiguous sequence of 8 amino acids prepared by multipin peptide synthesis. The horizontal axis represents the various polypeptides and the numbers of amino acid residues in SEQ ID NO: 1, while the vertical axis represents absorbance.
Figure 3:
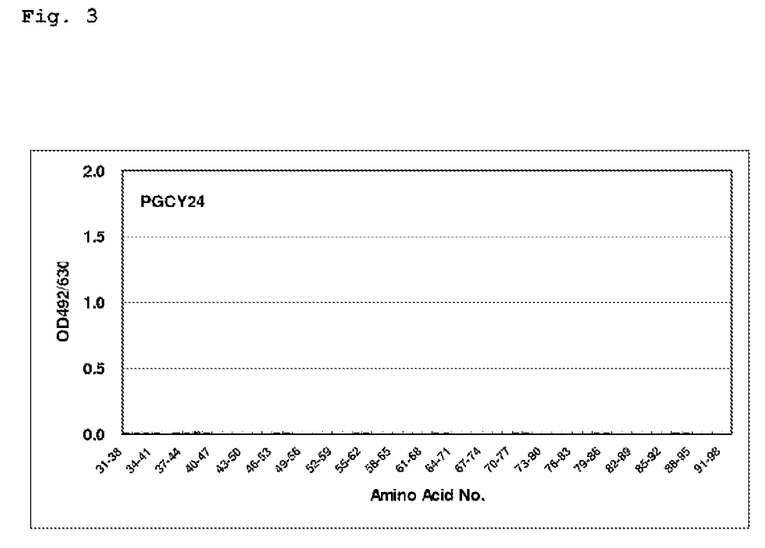
FIG. 3 is a graph showing the binding ability of monoclonal antibody PGCY24 to various polypeptides each having a contiguous sequence of 8 amino acids prepared by multipin peptide synthesis. The horizontal axis represents the various polypeptides and the numbers of amino acid residues in SEQ ID NO: 1, while the vertical axis represents absorbance.
Figure 4:
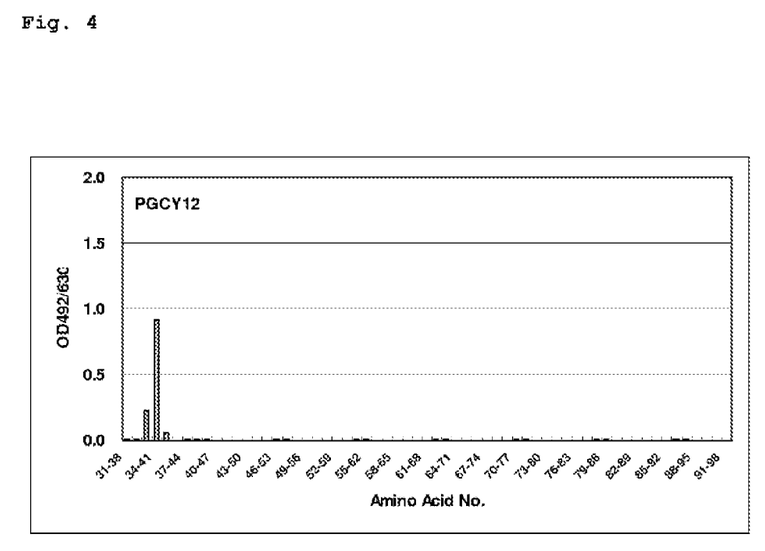
FIG. 4 is a graph showing the binding ability of monoclonal antibody PGCY12 to various polypeptides each having a contiguous sequence of 8 amino acids prepared by multipin peptide synthesis. The horizontal axis represents the various polypeptides and the numbers of amino acid residues in SEQ ID NO: 1, while the vertical axis represents absorbance.
Figure 5:
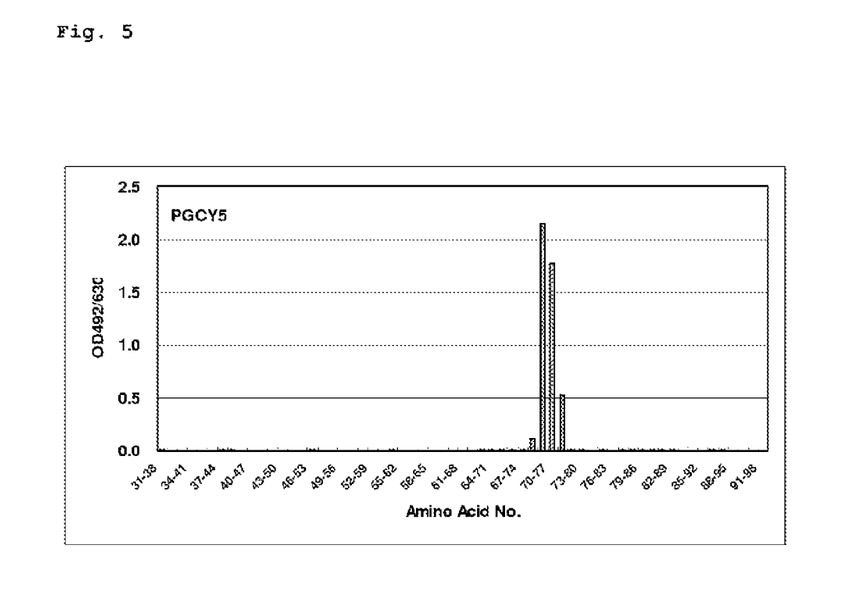
FIG. 5 is a graph showing the binding ability of monoclonal antibody PGCY5 to various polypeptides each having a contiguous sequence of 8 amino acids prepared by multipin peptide synthesis. The horizontal axis represents the various polypeptides and the numbers of amino acid residues in SEQ ID NO: 1, while the vertical axis represents absorbance.

As shown in FIG. 1, it was confirmed that the monoclonal antibody PGCY9 binds very weakly to ProGRP (57-64). Furthermore, as shown in FIG. 2 and FIG. 3, it was confirmed that the monoclonal antibodies PGCY17 and PGCY24 do not bind to a polypeptide having contiguous 8 amino acids in the amino acid sequence of ProGRP (31-98). From this, it is speculated that PGCY17 and PGCY24 recognize not a contiguous sequence of 8 amino acids, but an epitope represented by a polypeptide having a sequence of more than 8 amino acids. On the other hand, as shown in FIG. 4, it was confirmed that the monoclonal antibody PGCY12 was strongly bound to ProGRP (34-41) and was weakly bound to ProGRP (33-40) and ProGRP (35-42). Therefore, it is speculated that PGCY12 recognizes the epitope represented by the amino acid sequence consisting of amino acid 34 to amino acid 41 of ProGRP. Furthermore, it was confirmed that the monoclonal antibody PGCY5 was strongly bound to ProGRP (69-76) and ProGRP (70-77), was bound to ProGRP (71-78), and was very weakly bound to ProGRP (68-75). Therefore, it is speculated that the monoclonal antibody PGCY5 recognizes a common epitope represented by the amino acid sequence consisting of amino acid 69 to amino acid 76, and the amino acid sequence consisting of amino acid 70 to amino acid 77 of ProGRP.

(3) The polypeptides having partial amino acid sequences of ProGRP (31-98) as indicated in Table 1 were synthesized by an Fmoc method and purified. BSA was dissolved to a concentration of 20 µg/mL in PBS containing 6 M urea dissolved therein, and 100 µL of the solution was added to each well of a 96-well microtiter plate (NUNC, Maxisorp). The plate was incubated for 3 hours at room temperature. Each well was washed five times with PBS, and a solution prepared by dissolving N-(3-dimethylaminopropyl)-N'-ethyl carbodiimide hydrochloride (EDC) and N-hydroxysuccimide (NHS) in PBS to a concentration of 1 mg/mL, respectively, was added to each well in an amount of 100 µL. The plate was incubated for 2 hours at room temperature to thereby activate the carboxyl group of BSA immobilized to the well. Each well was washed three times with PBS, and the respective polypeptides were diluted with a 0.1 M phosphate buffer solution (pH 6.0) to a concentration of 5 µg/mL. 100 µl, each of the dilutions were added to each well of a 96-well microtiter plate, and the plate was incubated overnight at 4° C. Thereby, the respective polypeptides were bound to the immobilized BSA via an amino group.

Each well was washed two times with PBS, and then PBS containing 1% BSA and 2% sucrose was added to each well in an amount of 350 µL. The plate was incubated for 3 hours at room temperature, and thereafter, PBS was removed by suction. The respective monoclonal antibodies diluted to a concentration of 1 µg/mL were added to each well in an amount of 100 µL, and the plate was allowed to react for 60 minutes at room temperature. Subsequently, each well was washed five times with PBS containing 0.05% TWEEN 20™ (polyoxyethylene (20) sorbitan monolaurate) (PBS-T), and then 100 µL of a horseradish peroxidase (HRP)-labeled anti-mouse IgG antibody solution was added to each well to allow a reaction for 20 minutes at room temperature. Each well was washed five times with PBS-T, and then a substrate solution (0.1 M citrate phosphate buffer solution containing 2 mg/mL of ortho-phenylenediamine and 0.9 µL/mL of a 30% aqueous solution of hydrogen peroxide, pH 5.0) was added to each well in an amount of 100 µL. The plate was allowed to react for 20 minutes at room temperature, and then 100 µL of 2 N sulfuric acid was added to each well to terminate the reaction. Immediately, the absorbance at 492 nm was measured. In addition to the respective monoclonal antibodies of the present invention, the polypeptide having an amino acid sequence consisting of amino acid 40 to amino acid 60 of ProGRP as shown in Patent Document 3 was recognized, and the epitope of GRP-3D6-2, which is a monoclonal antibody that does not respond to a polypeptide having a contiguous sequence of 8 amino acids, was also investigated at the same time. The results are presented in Table 1.

TABLE 1

| Peptide | Monoclonal antibody (OD492/620) | | | |
|---|---|---|---|---|
| aa No. | PGCY9 | PGCY17 | PGCY24 | GRP-3D6-2 |
| 31-52 | 0.008 | 0.008 | 0.008 | 0.008 |
| 42-53 | 0.009 | 0.008 | 0.008 | 0.009 |
| 44-55 | 0.005 | 0.004 | 0.003 | 0.004 |
| 45-57 | 0.004 | 0.004 | 0.004 | 0.003 |
| 46-59 | 0.004 | 0.017 | 0.010 | 0.006 |
| 47-61 | 0.004 | 0.074 | 0.057 | 0.082 |
| 55-66 | 0.134 | 0.003 | 0.005 | 0.002 |
| 57-68 | 0.239 | 0.004 | 0.002 | 0.003 |
| 40-60 | 0.003 | 0.160 | 0.156 | 0.097 |
| 44-62 | 0.040 | 0.297 | 0.269 | 0.243 |
| 54-78 | 0.376 | 0.004 | 0.003 | 0.004 |
| 54-90 | 0.399 | 0.004 | 0.004 | 0.003 |
| 70-90 | 0.008 | 0.006 | 0.008 | 0.007 |
| 31-98 | 3.304 | 1.391 | 1.041 | 1.624 | aa No.: amino acid number

It could be verified, as shown in Table 1, that the examined 4 species of monoclonal antibodies specifically recognize the polypeptides having partial amino acid sequences of ProGRP, and that the not all of the monoclonal antibodies bind to ProGRP (42-53). Furthermore, the monoclonal antibody PGCY9 was relatively strongly bound to ProGRP (55-66), ProGRP (57-68), ProGRP (54-78) and ProGRP (54-90). Furthermore, the monoclonal antibodies PGCY17 and PGCY24 were relatively strongly bound to ProGRP (47-61), ProGRP (40-60) and ProGRP (44-62), but were very weakly bound to ProGRP (46-59). The monoclonal antibody GRP-3D6-2 was relatively strongly bound to ProGRP (47-61), ProGRP (40-60) and ProGRP (44-62).

(4) The recombinant ProGRP (31-98) produced in Example 1 was diluted in PBS to a concentration of 1 µg/mL, and 50 µL of the dilution was added to each well of a 96-well microtiter plate (NUNC, Maxiorp). The plate was incubated overnight at 4° C. Each well was washed two times with PBS, and PBS containing 0.5% casein sodium and 2% sucrose (pH 7.1) was added to each well in an amount of 350 µL. The plate was incubated for 3 hours at room temperature, and then the buffer solution was removed by suction. A solution prepared by diluting each of the peptides with a reaction solution (0.1 M sodium phosphate buffer solution containing 1% BSA, 0.05% casein sodium, 1% polyvinylpyrrolidone, 10 mM EDTA-2Na, 0.15 M NaCl and 0.05% TWEEN 20™ (polyoxyethylene (20) sorbitan monolaurate), pH 7.2) to a concentration of 2 µg/mL, was added to each well in an amount of 50 µL. Subsequently, each of the monoclonal antibodies diluted to a concentration of 1 µg/mL was added to each well in an amount of 50 µL, and the plate was incubated for 60 minutes at room temperature. In this process, immobilized ProGRP (31-98) and each peptide in the solution compete with each other, and then a binding reaction with each monoclonal antibody was done. Thereafter, each well was washed five times with PBS containing 0.05% TWEEN 20™ (polyoxyethylene (20) sorbitan monolaurate) (PBS-T), and then 100 µL of a horseradish peroxidase (HRP)-labeled anti-mouse IgG antibody solution was added to each well to react for 20 minutes at room temperature. Each well was washed five times with PBS-T, and then 100 µL of a substrate solution (0.1 M citrate phosphate buffer solution containing 2 mg/mL of ortho-phenylenediamine and 0.9 µL/mL of a 30% aqueous solution of hydrogen peroxide, pH 5.0) was added to each well. The plate was allowed to react for 20 minutes at room temperature, and then 100 µL of 2 N sulfuric acid was added to each well to terminate the reaction. The absorbance at 492 nm was measured. The inhibition rates (%) calculated by taking the absorbance of a well which did not contain the peptide (control) as 100%, are presented in Table 2.

TABLE 2

| Peptide | Monoclonal antibody (inhibition rate %) | | | |
|---|---|---|---|---|
| aa No. | PGCY9 | PGCY17 | PGCY24 | GRP-3D6-2 |
| 31-52 | 0.0 | 0.0 | 0.0 | 0.0 |
| 42-53 | 0.0 | 0.0 | 0.0 | 2.3 |
| 44-55 | 0.0 | 15.8 | 14.0 | 18.7 |
| 45-57 | 0.0 | 89.8 | 86.0 | 38.8 |
| 46-59 | 0.0 | 98.5 | 97.6 | 88.6 |
| 47-61 | 0.0 | 96.6 | 81.6 | 93.1 |
| 55-66 | 91.1 | 6.5 | 0.0 | 15.3 |
| 57-68 | 25.3 | 0.0 | 0.0 | 9.6 |
| 40-60 | 0.0 | 97.0 | 96.2 | 92.4 |
| 44-62 | 17.3 | 99.2 | 99.5 | 99.4 |
| 54-78 | 96.3 | 17.7 | 0.0 | 19.5 |
| 54-90 | 89.2 | 0.0 | 0.0 | 11.9 |
| 70-90 | 0.0 | 0.0 | 0.0 | 0.0 |
| 82-96 | 0.0 | 0.0 | 0.0 | 0.0 |
| 31-98 | 96.0 | 96.7 | 93.4 | 94.8 | aa No.: amino acid number

As shown in Table 2, it was verified that the binding of each monoclonal antibody to the immobilized polypeptides was all inhibited to a level of 90% or greater in the presence of ProGRP (31-98), and was all not inhibited in the presence of ProGRP (42-53). For the monoclonal antibody PGCY9, the polypeptides verified to have binding inhibition to a level of 80% or greater were ProGRP (55-66), ProGRP (54-78) and ProGRP (54-90). For the monoclonal antibodies PGCY17 and PGCY24, the polypeptides verified to have binding inhibition to a level of 80% or greater were ProGRP (45-57), ProGRP (46-59), ProGRP (47-61), ProGRP (40-60) and ProGRP (44-62). In addition, the polypeptides verified to have binding inhibition to a level of 80% or greater with the monoclonal antibody GRP-3D6-2 were ProGRP (46-59), ProGRP (47-61), ProGRP (40-60) and ProGRP (44-62), and the binding to ProGRP (45-57) for which the inhibitory activity of PGCY17 or PGCY24 was verified, was weakly inhibited.

The monoclonal antibody PGCY9 was bound to ProGRP (55-66) and ProGRP (57-68) as described in section (3) above, and was more strongly bound to ProGRP (57-68) than to ProGRP (55-66). Furthermore, in section (4), sufficient inhibition was exerted with ProGRP (55-66), and a weak inhibition reaction was recognized with ProGRP (57-68). Therefore, it is believed that the monoclonal antibody PGCY9 recognizes the epitope represented by the amino acid sequence consisting of amino acid 55 to amino acid 68 of ProGRP.

From the results of epitope analysis in sections (3) and (4), it is speculated that the monoclonal antibodies PGCY17 and PGCY24 recognize the epitope represented by the amino acid sequence consisting of amino acid 47 to amino acid 57 of ProGRP. It is also conceived that the monoclonal antibody GRP-3D6-2 is related to an epitope which is represented by an amino acid sequence consisting of amino acid 47 to amino acid 59 of ProGRP located closer to the C-terminal side than the epitope for PGCY17 or PGCY24. Further, the epitope which the monoclonal antibody PGCY5 and monoclonal antibody PGCY12 can recognize is a contiguous epitope formed from a contiguous sequence of 8 amino acids. It was also speculated that the monoclonal antibodies PGCY17 and PGCY24 do not bind to a polypeptide having a contiguous sequence of 8 amino acids within ProGRP (31-98), but recognize an epitope represented by a contiguous sequence of 11 amino acids of ProGRP (47-57). The epitopes suspected to be recognized by the respective monoclonal antibodies are presented in Table 3.

TABLE 3

| Monoclonal antibody | Epitope (aa No.) |
|---|---|
| PGCY9 | 55-68 |
| PGCY17 | 47-57 |
| PGCY24 | 47-57 |
| PGCY12 | 34-41 |
| PGCY5 | 70-76 |
| GRP-3D6-2 | 47-59 |

Example 3

The various monoclonal antibodies of the present invention and the monoclonal antibody GRP-3G2 shown in Example 6 and 7 of Japanese Patent No. 3210994 were used to attempt identification of ProGRP partial peptides that were stable during storage of test samples such as serum. Here, the monoclonal antibody GRP-3G2 is an antibody that recognizes an epitope represented by the amino acid sequence consisting of amino acid 84 to amino acid 88 of ProGRP, as shown in Patent Document 3.

Eight test samples A to H which had been stored frozen and at 4° C. for 1, 4 and 7 days, respectively, were subjected to analysis as described below. Each of the monoclonal antibodies (PGCY17, PGCY9 and GRP-3G2) was added to each well of a 96-well microplate in an amount of 100 µL a concentration of 4 µg/mL, and the plate was incubated overnight at 4° C. Each well was washed two times with a 10 mM phosphate buffer solution (pH 7.3) containing 0.15 M NaCl, and then 350 µL of a blocking solution (10 mM phosphate buffer solution containing 0.5% casein sodium and 2% sucrose, pH 7.1) was added. The plate was kept still standing for 2 hours. After the blocking solution was removed, 100 µL of a reaction solution (0.1 M sodium phosphate buffer solution containing 1% BSA, 0.05% casein sodium, 1% polyvinylpyrrolidone, 10 mM EDTA-2Na, 0.15 M NaCl and 0.05% TWEEN 20™ (polyoxyethylene (20) sorbitan monolaurate), pH 7.2) and 50 µL of an analysis test sample were added to each well, and the plate was allowed to react for one hour at 37° C. Each well was washed five times with a washing solution (10 mM phosphate buffer solution containing 0.05% TWEEN 20™ (polyoxyethylene (20) sorbitan monolaurate), pH 7.3), and 100 µL of a solution of each monoclonal antibody (PGCY12, PGCY17, PGCY9 and PGYC5) labeled with HRP was added thereto to react for 30 minutes at room temperature. Each well was washed five times with the washing solution, and was added 100 µL of a substrate solution (0.1 M citrate phosphate buffer solution containing 2 mg/mL of ortho-phenylenediamine and 0.9 µL/mL of a 30% aqueous solution of hydrogen peroxide, pH 5.0). The plate was incubated for 30 minutes, and 100 µL of 2 N sulfuric acid was added to terminate the enzymatic reaction. The absorbance at 492 nm (reference wavelength 620 nm) in each well was measured with a microplate reader.

Figure 6:
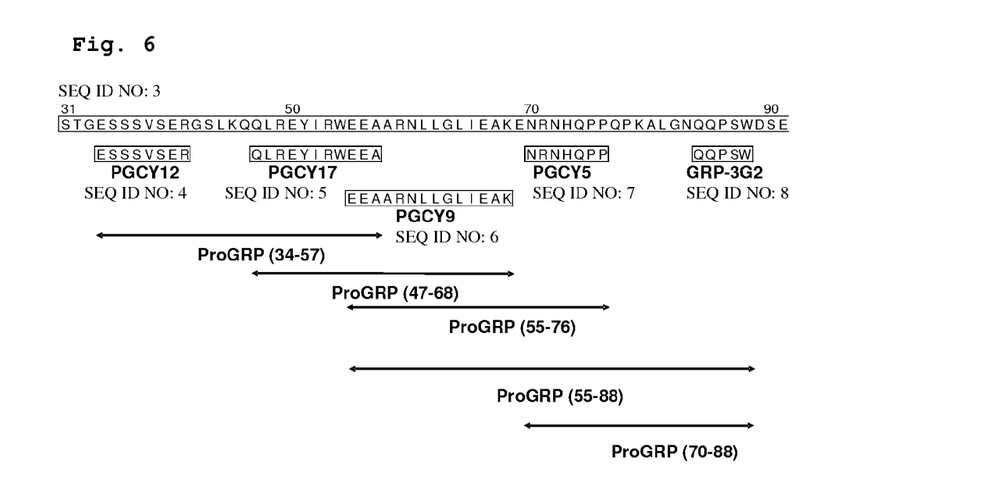
FIG. 6 is a schematic diagram showing ProGRP (31-98) and the positional relationship of the epitopes recognized by various monoclonal antibodies.

The partial amino acid sequence of a partial digested product of ProGRP existing in a test sample can be estimated when the antibodies which have a different recognition site are combined as the antibody for the solid phase and the labeled antibody. The combinations of the antibodies used this time are presented in FIG. 6. When the monoclonal antibodies PGCY12 and PGCY17 are combined, a digested product having an amino acid sequence consisting of amino acid 34 to amino acid 57 of ProGRP among the ProGRP digests in the test sample can be measured. Similarly, a digested product having an amino acid sequence consisting of amino acid 47 to amino acid 68 of ProGRP can be measured with a combination of PGCY17 and PGCY9, and a digested product having an amino acid sequence consisting of amino acid 55 to amino acid 76 of ProGRP can be measured with a combination of PGCY9 and PGCY5. A digested product having an amino acid sequence consisting of amino acid 55 to amino acid 88 of ProGRP can be measured with a combination of PGCY9 and GRP-3G2, and a digested product having an amino acid sequence consisting of amino acid 70 to amino acid 88 of ProGRP can be measured with a combination of PGCY5 and GRP-3G2.

The measured values for ProGRP in the test samples stored at 4° C. for 1, 4 and 7 days, as calculated by taking the measured values for ProGRP in the test samples stored frozen as 100%, are presented in Table 4.

TABLE 4

| | | Labeled antibody | | | | |
|---|---|---|---|---|---|---|
| | | PGCY12 | PGCY17 | PGCY5 | PGCY9 | PGCY5 |
| | | Immobilized antibody | | | | |
| | 4° C. | PGCY17 | PGCY9 | PGCY9 | GRP-3G2 | GRP-3G2 |
| Sample | storage period | Peptide region recognizable by combined antibodies | | | | |
| | | 34-57 | 47-68 | 55-76 | 55-88 | 70-88 |
| A | 0 time | 100.0 | 100.0 | 100.0 | 100.0 | 100.0 |
| | 1 day | 105.2 | 100.5 | 100.2 | 88.6 | 85.4 |
| | 4 days | 102.6 | 101.0 | 99.6 | 74.6 | 73.4 |
| | 7 days | 99.1 | 96.9 | 95.5 | 67.0 | 63.1 |
| B | 0 time | 100.0 | 100.0 | 100.0 | 100.0 | 100.0 |
| | 1 day | 103.7 | 98.1 | 99.3 | 96.0 | 88.8 |
| | 4 days | 109.4 | 92.3 | 94.5 | 79.3 | 75.7 |
| | 7 days | 118.7 | 90.4 | 90.6 | 66.2 | 66.8 |
| C | 0 time | 100.0 | 100.0 | 100.0 | 100.0 | 100.0 |
| | 1 day | 109.3 | 97.3 | 96.8 | 88.9 | 86.1 |
| | 4 days | 101.4 | 93.6 | 91.0 | 66.7 | 59.4 |
| | 7 days | 92.0 | 83.0 | 81.3 | 49.9 | 45.3 |
| D | 0 time | 100.0 | 100.0 | 100.0 | 100.0 | 100.0 |
| | 1 day | 105.0 | 96.3 | 98.8 | 86.0 | 92.5 |
| | 4 days | 101.6 | 90.1 | 92.1 | 68.5 | 75.0 |
| | 7 days | 107.4 | 89.2 | 85.2 | 60.5 | 74.5 |
| E | 0 time | 100.0 | 100.0 | 100.0 | 100.0 | 100.0 |
| | 1 day | 97.4 | 100.8 | 95.2 | 82.7 | 78.6 |
| | 4 days | 82.4 | 92.3 | 85.3 | 63.1 | 55.6 |
| | 7 days | 85.6 | 87.4 | 81.9 | 51.0 | 48.5 |
| F | 0 time | 100.0 | 100.0 | 100.0 | 100.0 | 100.0 |
| | 1 day | 101.2 | 98.2 | 96.5 | 89.7 | 88.5 |
| | 4 days | 100.7 | 89.6 | 85.6 | 75.6 | 75.0 |
| | 7 days | 95.4 | 82.1 | 78.0 | 62.0 | 69.4 |
| G | 0 time | 100.0 | 100.0 | 100.0 | 100.0 | 100.0 |
| | 1 day | 99.3 | 99.5 | 98.5 | 79.8 | 89.4 |
| | 4 days | 90.8 | 94.5 | 93.3 | 64.7 | 62.1 |
| | 7 days | 77.7 | 85.8 | 82.8 | 45.9 | 50.0 |
| H | 0 time | 100.0 | 100.0 | 100.0 | 100.0 | 100.0 |
| | 1 day | 105.7 | 104.0 | 103.7 | 96.8 | 98.1 |
| | 4 days | 109.9 | 96.6 | 96.3 | 85.0 | 85.4 |
| | 7 days | 114.4 | 90.5 | 85.2 | 72.5 | 79.3 |

In regard to the combination of the monoclonal antibodies PGCY9 and GRP-3G2 and the combination of monoclonal antibodies PGCY5 and GRP-3G2, an immunoactivity of 85% or greater was retained after storage for 1 day in most of the test samples, but the immunoactivity of all of the test samples was decreased to 55 to 85% after storage for 4 days, and to 80% or lower after storage for 7 days. This is believed to be a loss of immunoactivity due to cleavage of ProGRP on the C-terminal side at Lys-79 of SEQ ID NO: 1 by the proteases in the blood during the storage period or the like, as disclosed in Patent Document 3.

In regard to the combination of the monoclonal antibodies PGCY12 and PGCY17, the combination of the monoclonal antibodies PGCY17 and PGCY9, and the combination of the monoclonal antibodies PGCY5 and PGCY9, the immunoactivity was maintained relatively stable; however, in the combination of PGCY12 and PGCY17, the immunoactivity was increased by storage in two test samples (B and H) among the 8 test samples, and the immunoactivity exceeded 110% after storage for 7 days.

When the combination of the monoclonal antibodies PGCY17 and PGCY9 is compared with the combination of the monoclonal antibodies PGCY5 and PGCY9, the immunoactivity of 4 test samples in the latter combination was decreased to 85% or lower after storage for 7 days. On the other hand, in the former combination, an immunoactivity of 80% or greater was maintained in all of the test samples after storage for 7 days, and 6 out of the 8 test samples retained an immunoactivity of 85% or greater. This implies that a digest of ProGRP determined by combining the monoclonal antibodies PGCY17 and PGCY9 undergoes less deterioration when the test sample is stored at 4° C. and is more advantageous as an object of analysis, as compared with a digest of ProGRP measured according to the method described in Patent Document 3.

Example 4

In the method described in Example 4 of Patent Document 3, the antibodies were changed to a combination of the monoclonal antibodies PGCY17 and PGCY9, and the time for measurement, amount of test sample to be measured, and measurable sensitivity necessitated by the method utilizing the same combination of monoclonal antibodies were examined.

To each well of a 96-well microplate, 120 µL of a solution prepared by dissolving the monoclonal antibody PGCY9 in an antibody fixing solution (0.1 M carbonate buffer solution containing 0.6 M NaCl, pH 9.6) to a concentration of 5 µg/mL was added, and the plate was incubated overnight at 4° C. Each well was washed two times with a 10 mM phosphate buffer solution (pH 7.3) containing 0.15 M NaCl, and then 350 µL of a blocking solution (10 mM phosphate buffer solution containing 0.5% casein sodium and 5% sucrose, pH 7.1) was added thereto. The plate was kept still standing for 2 hours to achieve blocking. The blocking solution was removed, and then the plate was dried. After drying, 100 µL of a reaction solution (0.1 M potassium phosphate buffer solution containing 1% BSA, 1% polyvinylpyrrolidone, 0.05% casein sodium, 0.05% TWEEN 20™ (polyoxyethylene (20) sorbitan monolaurate), 0.1% TRITON™ X-100 (polyoxyethylene octyl phenyl ether), 0.15 M NaCl, 10 mM EDTA-2Na and 40 µg/mL of mouse IgG, pH 7.0) and 25 µL of a test sample were added to each well, and the plate was allowed to react for one hour at 37° C. Each well was washed five times with a washing solution (10 mM phosphate buffer solution containing 0.05% TWEEN 20™ (polyoxyethylene (20) sorbitan monolaurate), pH 7.3), and 200 µL of a solution prepared by dissolving HRP-labeled Fab' of PGCY17 in a labeled-antibody diluting solution (0.1 M potassium phosphate buffer solution containing 2% BSA, 0.25% polyvinylpyrrolidone, 0.05% TWEEN 20™ (polyoxyethylene (20) sorbitan monolaurate), 0.05% casein sodium, 0.15 M NaCl, 1% sucrose and 25 µg/mL of mouse IgG, pH 6.5) was added to react for 20 minutes at room temperature. Each well was washed five times with the washing solution, and 100 µL of a substrate solution (0.1 M citrate phosphate buffer solution containing 2 mg/mL of ortho-phenylenediamine and 0.9 µL/mL of a 30% aqueous solution of hydrogen peroxide, pH 5.0) was added thereto. The plate was incubated for 20 minutes, and 100 µL of 2 N sulfuric acid was added to terminate the enzymatic reaction. The absorbance at 492 nm (reference wavelength 620 nm) was measured with a microplate reader. A standard curve therefor is presented in FIG. 7.

Figure 7:
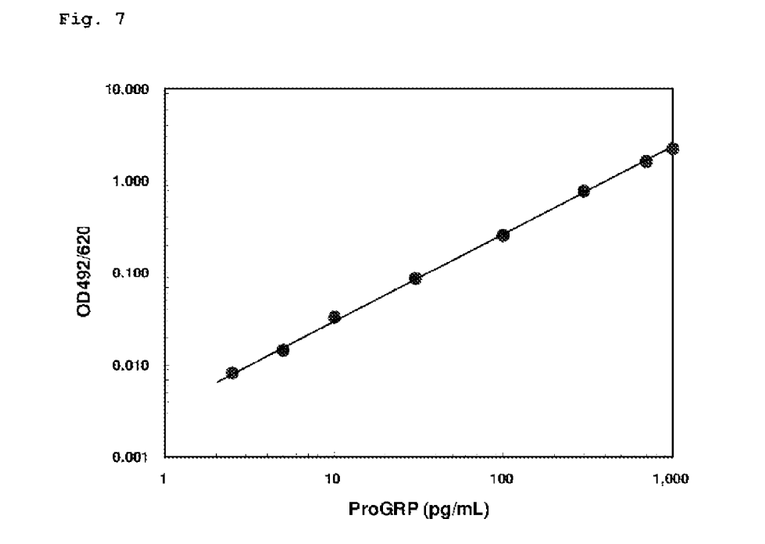
FIG. 7 is a standard curve for the measurement method making use of PGCY9 and PGCY17, which are antibodies that bind to a partial peptide consisting of amino acid 47 to amino acid 68. The horizontal axis represents the concentration of ProGRP, while the vertical axis represents absorbance.

As a result, it was verified that the method of the present invention can detect about 2.5 pg/mL of ProGRP, despite a total reaction time of 100 minutes and the amount of sample being as small as 25 µL. This sensitivity is sufficient for detecting the ProGRP concentration in a test sample obtained from a normal person. Furthermore, when the method is compared with the method described in Example 4 of Patent Document 3, the time for measurement is shortened from 120 minutes to 100 minutes, and the amount of test sample for measurement is reduced to ¼, while the detective sensitivity is increased to about 1.7-fold.

Example 5

50 µL, of a solution prepared by dissolving a goat anti-mouse IgG (Fc) (Jackson Immuno Research) antibody in a 0.1 M carbonate buffer solution (pH 9.6) containing 0.5 M NaCl, to a concentration 2.5 µg/mL, was added to each well of a 96-well microplate, and the plate was incubated overnight at 4° C. Each well was washed two times with 10 mM phosphate buffer solution (pH 7.3) containing 0.15 M NaCl, and then 350 µL, of a blocking solution (10 mM phosphate buffer solution containing 0.5% casein sodium and 2% sucrose, pH 7.1) was added thereto. The plate was kept still standing for 2 hours. The blocking solution was removed, and then the plate was dried at room temperature. 100 µL, of a solution prepared by diluting each monoclonal antibody in a reaction solution (0.1 M sodium phosphate buffer solution containing 1% BSA, 0.05% casein sodium, 1% polyvinylpyrrolidone, 10 mM EDTA-2Na, 0.15 M NaCl and 0.05% TWEEN 20™ (polyoxyethylene (20) sorbitan monolaurate), pH 7.2) at a concentration of 5 µg/mL, was added to each well to react for 2 hours at 37° C. This reaction allows the Fc portion of each monoclonal antibody to bind to the goat anti-mouse IgG (Fc) in a solid phase.

Subsequently, each well was washed five times with a washing solution (10 mM phosphate buffer solution containing 0.05% TWEEN 20™ (polyoxyethylene (20) sorbitan monolaurate), pH 7.3), and 100 µL of a reaction solution (0.1 M sodium phosphate buffer solution containing 1% BSA, 0.05% casein sodium, 1% polyvinylpyrrolidone, 10 mM EDTA-2Na, 0.15 M NaCl and 0.05% TWEEN 20™ (polyoxyethylene (20) sorbitan monolaurate), pH 7.2) and 50 µL of a solution of biotinylated recombinant ProGRP (31-98) (0 pg/mL, 200 pg/mL or 1000 pg/mL) were added to each well to react for one hour at 37° C. This reaction allows each monoclonal antibody to bind to the biotinylated recombinant ProGRP (31-98).

Each well was washed four times with a washing solution (10 mM phosphate buffer solution containing 0.05% TWEEN 20™ (polyoxyethylene (20) sorbitan monolaurate), pH 7.3), and 100 µL of a solution of HRP-labeled avidin D (Vector) diluted with a reaction solution (0.1 M sodium phosphate buffer solution containing 1% BSA, 0.05% casein sodium, 1% polyvinylpyrrolidone, 10 mM EDTA-2Na, 0.15 M NaCl and 0.05% TWEEN 20™ (polyoxyethylene (20) sorbitan monolaurate), pH 7.2) was added to react for 30 minutes at room temperature. Each well was washed four times with the washing solution, and 100 µL of a substrate solution (0.1 M citrate phosphate buffer solution containing 2 mg/mL of ortho-phenylenediamine and 0.9 µL/mL of a 30% aqueous solution of hydrogen peroxide, pH 5.0) was added thereto. The plate was incubated for 30 minutes, and 100 μL of 2 N sulfuric acid was added to terminate the enzymatic reaction. The absorbance at 492 nm (reference wavelength 630 nm) was measured with a microplate reader. The results are presented in FIG. 8.

Figure 8:
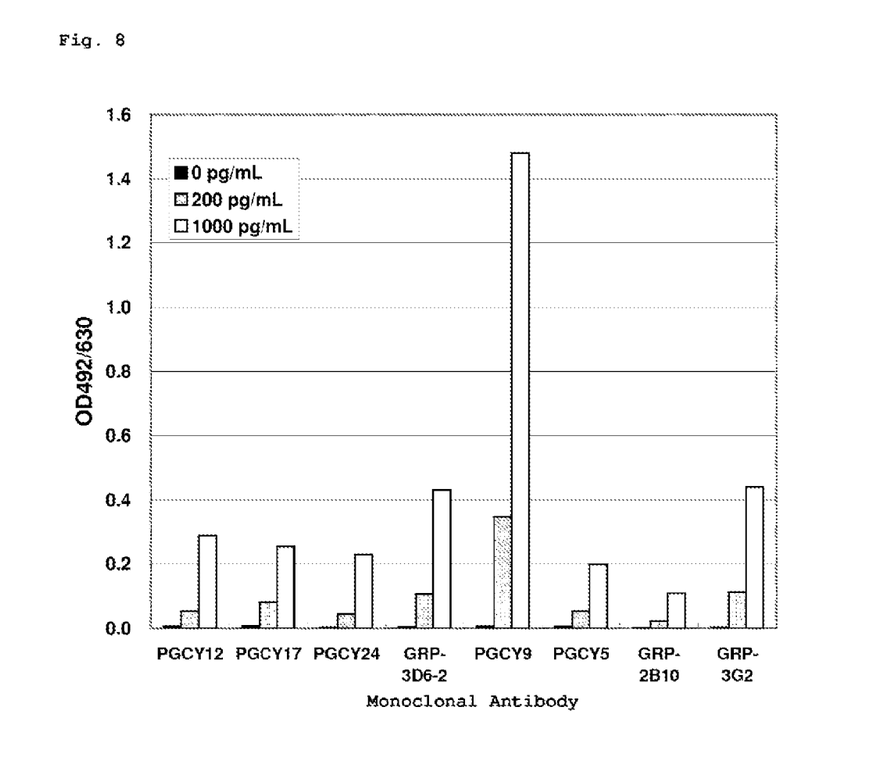
FIG. 8 is a graph showing the reactivity of biotinylated ProGRP with various monoclonal antibodies directed to ProGRP, which are bound to a solid phase of a microplate via an anti-mouse IgG (Fc) antibody. The horizontal axis represents the various monoclonal antibodies, while the vertical axis represents absorbance.

Among these monoclonal antibodies, the monoclonal antibody PGCY9 which binds to ProGRP (55-68) exhibits the highest reactivity, and even when compared with the monoclonal antibody GRP-3D6-2 used for the solid phase in Example 4 of Patent Document 3, the monoclonal antibody showed values that were about 3.3-fold higher. PGCY17 and PGCY24 which bind to ProGRP (47-57) exhibited almost the same reactivity, and GRP-3D6-2 that is capable of recognizing ProGRP (47-59) which is located slightly closer to the C-terminal side than PGCY17, exhibited higher reactivity compared to PGCY17. Furthermore, PGCY5 and GRP-2B10 that are capable of recognizing the vicinity of ProGRP (70-76) exhibited lower reactivity among these monoclonal antibodies, and GRP-3G2 that is capable of recognizing ProGRP (84-88), which is located closer to the C-terminal side than those, exhibited relatively higher reactivity. Based on the recognition site and reactivity of these monoclonal antibodies, it is thought that when use is made of a monoclonal antibody capable of recognizing an epitope represented by an amino acid sequence consisting of amino acid 55 to amino acid 68 of ProGRP, ProGRP or a digested product thereof in a test sample can be captured with high sensitivity. Furthermore, since the reactivity of PGCY5 and GRP-2B10 is low, it is believed that a monoclonal antibody capable of recognizing an epitope represented by an amino acid sequence consisting of amino acid 70 and the rest, has low reactivity. Thus, it is conceived that ProGRP or a digested product thereof can be captured with high sensitivity, also by using a monoclonal antibody capable of recognizing an epitope represented by an amino acid sequence consisting of amino acid 55 to amino acid 69 of ProGRP.

Example 6

(1) Biotinylation of Each Monoclonal Antibody 0.5 mg of each monoclonal antibody was added to 1 mL of a 0.1 M sodium phosphate buffer solution (pH 8.0), and Sulfo-NHS-Biotin (PIERCE) dissolved in dimethylformamide was added thereto at a molar ratio of IgG:Biotin=1:20. The mixture was mildly stirred for 60 minutes at room temperature. 100 μL of a 1.5 M glycine solution (pH 8.9) was added, and the mixture was mildly stirred for 10 minutes at room temperature. Gel filtration was performed using PBS as a solvent, and thus a biotinylated monoclonal antibody was obtained.

(2) Examination of Combination of Various Monoclonal Antibodies

100 μL of a solution prepared by dissolving each monoclonal antibody in an antibody fixing solution (0.1 M carbonate buffer solution containing 0.5 M NaCl, pH 9.6) at a concentration of 5 μg/mL, was added to each well of a 96-well microplate, and the plate was incubated overnight at 4° C. Each well was washed two times with 10 mM phosphate buffer solution (pH 7.3) containing 0.15 M NaCl, and then 350 μL of a blocking solution (10 mM phosphate buffer solution containing 0.5% casein sodium and 2% sucrose, pH 7.1) was added thereto. The plate was kept still standing for 2 hours to achieve blocking. The blocking solution was removed, and then 100 μL of a reaction solution (0.1 M sodium phosphate buffer solution containing 1% BSA, 0.05% casein sodium, 1% polyvinylpyrrolidone, 10 mM EDTA-2Na, 0.15 M NaCl and 0.05% TWEEN 20™ (polyoxyethylene (20) sorbitan monolaurate), pH 7.2) and 50 μL of recombinant ProGRP (0, 100, 500 or 2000 pg/mL) were added to each well to react for one hour at 37° C. Each well was washed five times with a washing solution (10 mM phosphate buffer solution containing 0.05% TWEEN 20™ (polyoxyethylene (20) sorbitan monolaurate), pH 7.3), and 100 μL of a solution prepared by dissolving each biotinylated monoclonal antibody in the reaction solution at a concentration of 1 μg/mL was added to react for 30 minutes at room temperature. 100 μL of a HRP-labeled avidin D (Vector) solution diluted with the reaction solution, was added thereto to react for 30 minutes at room temperature. Each well was washed five times with the washing solution, and 100 μL of a substrate solution (0.1 M citrate phosphate buffer solution containing 2 mg/mL of ortho-phenylenediamine and 0.9 μL/mL of a 30% aqueous solution of hydrogen peroxide, pH 5.0) was added thereto. The plate was incubated for 20 minutes, and 100 μL of 2 N sulfuric acid was added to terminate the enzymatic reaction. The absorbance at 492 nm (reference wavelength 600 nm) was measured with a microplate reader. The reactivity was classified into 5 grades (in a decreasing order, *: very highly reactive, ⊙: highly reactive, O: moderately reactive, Δ: slightly reactive, x: non-reactive), and the results are presented in Table 5.

TABLE 5

| Solid phase antibody | | Biotinylated antibody | | | | | | | |
|---|---|---|---|---|---|---|---|---|---|
| | | PGCY12 34-41 | PGCY17 47-57 | PGCY24 47-57 | GRP-3D6-2 47-59 | PGCY9 55-68 | PGCY5 70-76 | GRP-2B10 71-75 | GRP-3G2 84-88 |
| PGCY12 | 34-41 | X | O | O | X | X | X | X | Δ |
| PGCY 17 | 47-57 | O | X | X | X | ☆ | O | O | O |
| PGCY24 | 47-57 | Δ | X | X | X | O | X | X | X |
| GRP-3D6-2 | 47-59 | O | X | X | X | Δ | O | Δ | O |
| PGCY9 | 55-68 | O | ☆ | ☆ | X | X | ⊙ | O | ⊙ |
| PGCY5 | 70-76 | Δ | X | X | X | O | X | X | Δ |
| GRP-2B10 | 71-75 | X | Δ | X | X | Δ | X | X | Δ |
| GRP-3G2 | 84-88 | O | O | Δ | O | ⊙ | O | Δ | X |

☆: Very highly reactive
⊙: Highly reactive
O: Moderately reactive
Δ: Slightly reactive
X: Non-reactive As shown in Table 5, the reactivity could not be checked, first, for a combination of identical monoclonal antibodies, and for a combination of antibodies that were believed to recognize the same epitope, or to have the amino acid sequences representing the epitope largely overlapped with each other. When PGCY9 was immobilized, PGCY17 and PGCY24 among the biotinylated antibodies had the highest reactivity; GRP-3G2 and PGCY5 had the next higher reactivity, and GRP-2B10 and PGCY12 had the next high reactivity. The reactivity of GRP-3D6-2 could not be detected.

When PGCY17 was immobilized, PGCY9 among the biotinylated antibodies had the highest reactivity; and GRP-3G2, PGCY5, GRP-2B10 and PGCY12 had the next high reactivity. The reactivity of PGCY24 and GRP-3D6-2 could not be detected.

When PGCY24 was immobilized, PGCY9 among the biotinylated antibodies exhibited moderate reactivity, but other antibodies could hardly be detected the reactivity.

When GRP-3D6-2 was immobilized, GRP-3G2, PGCY5 and PGCY12 among the biotinylated antibodies exhibited slightly higher reactivity than GRP-2B10.

When PGCY9 was used as a biotinylated antibody, PGCY17 exhibited the highest reactivity as a solid phase antibody, while GRP-3G2 exhibited the next higher reactivity and PGCY24 and PGCY5 the next high reactivity.

Therefore, when PGCY9 that binds to ProGRP (55-68) is used as a solid phase antibody, and PGCY17 or PGCY24 that binds to ProGRP (47-57) is used as a labeled antibody which is the antibody on the detection side, or on the other hand, when PGCY17 or PGCY24 is used as a solid phase antibody, and PGCY9 is used as a labeled antibody which is the antibody on the detection side, high sensitivity determination of ProGRP or a digested product thereof can be carried out.

INDUSTRIAL APPLICABILITY

According to the method of the present invention, since a newly identified epitope on a digested product of ProGRP which is stably stored in a test sample, is used as an object of measurement, a detective sensitivity that is equivalent to that of conventional measurement methods may be obtained, the test sample is hardly affected upon handling of the test sample after collection, highly reproducible measured values are obtained, and the like. Thus, the method of the present invention is effective in the detection of ProGRP in the blood.

The invention claimed is:

1. A method for measuring a gastrin-releasing peptide precursor and/or a digested product thereof in a test sample, comprising:
   i) reacting a test sample with two or more different monoclonal antibodies which are capable of recognizing an epitope within an amino acid sequence consisting of amino acid 47 to amino acid 68 of SEQ ID NO:1, wherein at least one of the two or more different monoclonal antibodies is selected from the group consisting of (1) a monoclonal antibody produced by hybridoma GCY9 deposited under Accession No. FERM BP-10991 and (2) a monoclonal antibody produced by hybridoma GCY17 deposited under Accession No. FERM BP-10992, and
   ii) detecting an immunocomplex developed by step i), thereby detecting a gastrin-releasing peptide precursor and/or a digested product thereof in the test sample.

2. The method of claim 1, wherein the method is a sandwich immunoassay method.

3. The method of claim 1 wherein one of the two or more different monoclonal antibodies is a monoclonal antibody produced by hybridoma GCY9 deposited under Accession No. FERM BP-10991.

4. The method of claim 1 wherein one of the two or more different monoclonal antibodies is a monoclonal antibody produced by hybridoma GCY17 deposited under Accession No. FERM BP-10992.

5. The method of claim 1 wherein a kit is used for measuring the gastrin-releasing peptide precursor or the digested product thereof, the kit comprising the two or more different monoclonal antibodies.

* * * * *